United States Patent

Jung et al.

[11] Patent Number: 5,847,182
[45] Date of Patent: Dec. 8, 1998

[54] FLUORENYL SUBSTITUTED ORGANOSILANES AND THEIR PREPARATION METHODS

[75] Inventors: Il Nam Jung, Seoul; Bok Ryul Yoo, Koyang; Joon Soo Han; Yeon Seok Cho, both of Seoul, all of Rep. of Korea

[73] Assignee: Korea Institue of Science and Technology, Seoul, Rep. of Korea

[21] Appl. No.: 44,603

[22] Filed: Mar. 19, 1998

[30] Foreign Application Priority Data

Mar. 19, 1997 [KR] Rep. of Korea ............... 9346/1997
Oct. 22, 1997 [KR] Rep. of Korea ............. 54145/1997

[51] Int. Cl.⁶ .................................................. C07F 7/08
[52] U.S. Cl. ................................. 556/489; 556/466
[58] Field of Search .................................. 556/489, 466

[56] References Cited

U.S. PATENT DOCUMENTS 5,525,938  6/1996  Jung .
5,616,752  4/1997  Patsidis et al. .................. 556/489 X

OTHER PUBLICATIONS

R.M. Roberts and A.A. Khalaf, *Friedel–Crafts Alkylation Chemistry*, Marcel Dekker Inc., New York (1984).
R.H. Krieble and J.R. Elliott, *J. Am. Chem. Soc.*:67:1810 (1945).
Okuda, J. et al., *Organometallics* 14:789 (1995).
Bey, A.E. et al., *J. Org. Chem.* 31:2036 (1966).
D.H.V. Rasika, Z. Wang, S.G. Bott, *J. Organomet. Chem.* 508:91 (1996).
Q. Pei, Y. Yang, *J. Am. Chem. Soc.* 118:7416 (1996).

Primary Examiner—Paul F. Shaver
Attorney, Agent, or Firm—Darby & Darby

[57] ABSTRACT

The present invention relates to fluorenyl substituted organosilanes represented by the formula I and preparation methods thereof by reacting substituted biphenyls represented by the formul II with (dichloroalkyl)silanes represented by the formul III in the presence of Lewis acid catalysts such as aluminum chloride:

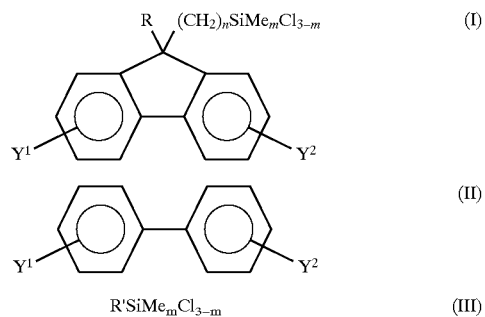

(wherein m is 0 or 1 and n is 0, 1, or 2. y1 and y2 represent hydrogen, bromo, phenyl and they can be same or different. R represents hydrogen or methyl group. $R_j^-$ can be dichloromethyl, 2,2-dichloroethyl, 3,3-dichloropropyl, 1,2-dichloroethyl, 2,3-dichloropropyl, 2,3-dichlorobutyl).

4 Claims, No Drawings

FLUORENYL SUBSTITUTED ORGANOSILANES AND THEIR PREPARATION METHODS

BACKGROUND OF THE INVENTION

1. Field of the Invention

The present invention relates to fluorenyl substituted organosilanes and preparation methods thereof.

2. Description of the Prior art

Since Friedel and Crafts first reported the alkylation reaction of benzene with alkyl halide in the presence of aluminum chloride catalyst in 1877, the Friedel-Crafts type alkylation reaction has been widely used as a synthetic procedure in organic synthesis(R. M. Roberts and A. A. Khalaf, *Friedel-Crafts Alkylation Chemistry*, Marcel Dekker, Inc., NY, 1984).

We also reported the Friedel-Crafts type alkylation of substituted benzenes with allyldichlorosilanes(Jung, I. N.; Yoo, B. R.; Lee, B. W.; Yeon, S. H., U.S. Pat. No. 5,527,938) and vinylchlorosilanes(Korea Patent Application #95-48114).

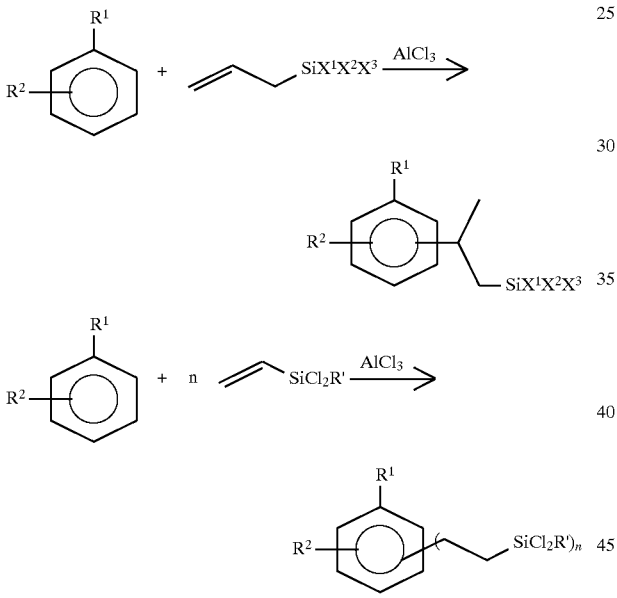

Recently, we reported the Friedel-Crafts type alkylation of substituted benzenes with (polychloroalkyl)silanes to (polyarylalkyl)silanes in the presence of Lewis acid catalysts such as aluminum chloride (Korea Patent Application No. 96-77559).

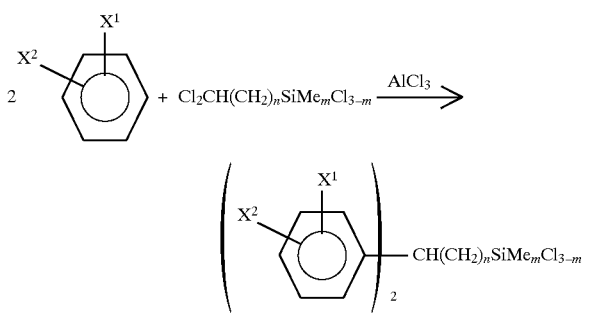

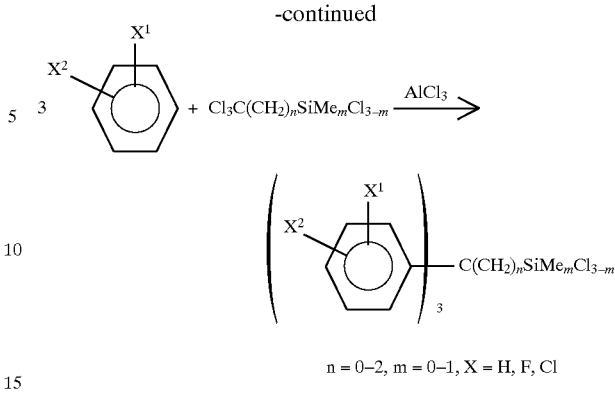

$n = 0-2, m = 0-1, X = H, F, Cl$ (Chloroalkyl)silanes can be easily prepared by the photochlorination of alkylsilanes on a large scale. In this process, polychlorinated alkylsilanes are inevitably produced as byproducts, because the chlorinated organic moieties are more susceptible toward the chlorination[R. H. Krieble and J. R. Elliott, *J. Am. Chem. Soc.*, 67,1810(1945)].

The present inventors found a new synthetic method for the cycloalkylation of biphenyl to fluorenyl substituted silane compounds during the studies of the Friedel-Crafts type alkylation of biphenyl with (dichloroalkyl)silanes. Fluorenyl substituted organosilanes are known to be the starting materials for the metallocene catalysts for olefin polymerizations[Okuda, J.; Schattenmann, F. J.; Wocadlo, S.; Massa, W. *Organometallics*, 14, 789(1995)] Fluorenyl substituted organosilanes have been prepared by reacting fluorene with alkyllithium and followed by coupling with trialkylchlorosilanes[Bey, A. E.; Weyenberg, D. R. *J. Org. Chem.*, 31, 2036(1966)].

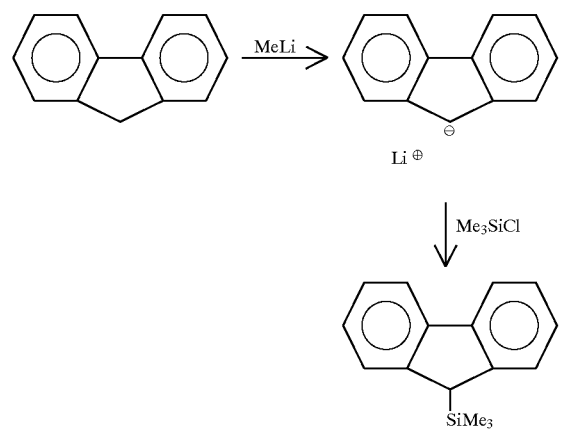

Similarly the fluorenyl anion can be coupled with haloalkyl containing trialkylsilanes to give fluorenylsilanes having an alkylene group between the fluorenyl and the silyl group[D. H. V. Rasika, Z. Wang, S. G. Bott, *J. Organomet. Chem.*, 508, 91(1996)]. However, this method can be only applied for the preparation of fluorenylsilanes having a trialkylsilyl group without halogen group on the silicon.

It is well known that fluorenyl compounds can be brominated at the carbon number 2 and 7 and then polymerized by debromocoupling to give polyfluorene products. Polyfluorenes are photo- and electroluminescent materials[Q. Pei, Y. Yang, *J. Am. Chem. Soc.* 118, 7416(1996)]. For the preparation of electroluminescent materials, fluorenyl compounds having two substituents on the carbon number 9. To derivatize 9 carbon expensive organometallic compounds should be used as described above.

BRIEF SUMMARY OF THE INVENTION

It is an object of the present invention to provide novel fluorenyl substituted organosilanes of the structural formula (I).

It is another object of the present invention to provide a preparation method of novel fluorenyl substituted organosilanes of the structural formula (I).

Other and further objects, features and advantages of the invention will appear more fully from the following description.

DETAILED DESCRIPTION OF THE INVENTION

The present invention relates to fluorenyl substituted organosilanes represented by the following formula (I) and preparation methods thereof by reacting substituted biphenyls represented by formula (II) with (dichloroalkyl)silanes represented by the formula (III) in the presence of Lewis acid catalysts such as aluminum chloride:

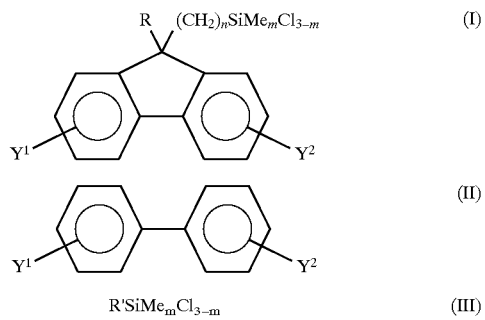

R'SiMe$_m$Cl$_{3-m}$ (III)

(wherein m is 0 or 1; n is 0, 1, or 2; $Y^1$ and $Y^2$ which can be same or different represent hydrogen, bromo, phenyl; R represents hydrogen or methyl group; R' can be dichloromethyl, 2,2-dichloroethyl, 3,3-dichloropropyl, 1,2-dichloroethyl, 2,3-dichloropropyl, 2,3-dichlorobutyl).

The preparation of fluorenyl group substituted organosilanes according to the present invention can be run in standard laboratory galsswares or commercial equipments, under inert atmosphere, with units for external heating and cooling, stirring, and for incremental addition of the start silanes. The reaction can be carried out in neat or in most of nonaromatic or nonprotic solvents such as hexane or cyclohexane. In a typical preparation, biphenyl represented by the formula II is placed in the reactor under inert atmosphere. Aluminum chloride or Aluminum is the best catalyst and can be used alone or in junction with other Lewis acid such as chlorides of zinc, boron, iron, tin, titanium and antimony in 2–10 mol percent relative to the reactants. The dichlorinated alkylsilane is then slowly added to the reactants in the reactor with stirring at the reaction temperatures between 0° C. and 200° C. for 2–20 hrs depending upon the reactants. After completion of addition, the solution may be kept stirring for a certain period of time to complete the alkylation and then the products may be crystallized from the solution or fractionally distilled at atmosphere or under vacuum.

The invention will be understood more readily with reference to the following examples; however, these examples are intended to illustrate the invention and are not to be construed to limit the scope of the invention.

EXAMPLES

Example 1

Reaction of biphenyl with (dichloromethyl)methyl dichlorosilane

To a 100 ml, three-necked, frame dried, round bottom flask equipped with a magnetic stirrer, a reflux condenser, and a dropping funnel, aluminum chloride 1.43 g (10.7 mmol) and biphenyl 16.5 g (107 mmol) were placed under dry nitrogen atmospheric pressure. After (dichloromethyl)methyldichlorosilane 7.50 ml (53.5 mmol) was added to the solution, the reaction mixture was heated for 2.5 hrs. at 120° C. The aluminum chloride catalyst was quenched with POCl$_3$ 1.04 ml (11.2 mmol) and then stirred for another 1 hr. to complete the deactivation. Freshly distilled hexane (100 ml) was added to the reaction mixture and insoluble solids in hexane were filtered from the organic solution. After hexane was distilled, the reaction products were vacuum distilled at 0.2 torr to give 8.79 g of 9-(methyldichlorosilyl)fluorene (bp; 115°–120° C./0.2 torr, yield; 59%).

H-NMR(CDCl3, ppm) 0.24(s, SiCH3, 3H), 4.26(s, CH, 1H), 7.38–8.00(m, ArH, 8H)

Example 2

Reaction of biphenyl with (1,2-dichloroethyl)-trichlorosilane

In a 250 ml, three-necked, frame dried, round bottom flask, aluminum 0.40 g (15 mmol), biphenyl 20.0 g (130 mmol), and (1,2-dichloroethyl)- trichlorosilane 7.50 ml (53.5 mmol) were reacted as in Example 1 at 120° C. for 30 min. Freshly distilled hexane (60 ml) was added to the reaction mixture and insoluble solids in hexane were filtered from the organic solution. After hexane was distilled, the reaction products were vacuum distilled to give 6.53 g of 9-(trichlorosilyl)methylfluorene (bp; 130°–135° C./0.2 torr, yield; 18%).

H-NMR(CDCl3, ppm) 2.24(d, J=6.4 Hz, SiCH2, 2H), 4.31(t, 6.4 Hz, CH, 1H), 7.26–7.79(m, ArH, 8H)

Example 3

Reaction of para-terphenyl with (2,2-dichloroethyl)-trichlorosilane

In the same apparatus and procedures as Example 1 above, 5.0 g (21.7 mmol) of para-terphenyl and 0.30 g (11.1 mmol) of aluminum were alkylated in CS$_2$ (50 ml) solution with (2,2-dichloroethyl)trichlorosilane 6.68 g (21.7 mmol) under dry nitrogen atmospheric pressure for 24 hrs at reflux temperature. Freshly distilled hexane (100 ml) was added to the reaction mixture and insoluble solids in hexane were filtered from the organic solution. After hexane and CS$_2$ were distilled, recrystallization from ether yielded 0.85 g of 9-(trichlorosilyl)methyl-2-phenylfluorene (yield; 10%).

H-NMR(CDCl3, ppm) 2.29(d, J=6.2 Hz, SiCH2, 2H), 4.39(t, 6.4 Hz, CH, 1H), 7.21–7.86(m, ArH, 12H)

Example 4

Reaction of meta-terphenyl with (2,2-dichloroethyl)-trichlorosilane

In the same apparatus and procedures as Example 1 above, 5.0 g (21.7 mmol) of meta-terphenyl and 0.47 g (17.4 mmol) of aluminum foil were alkylated in CS$_2$ (50 ml) solution with (2,2-dichloroethyl)-trichlorosilane 6.68 g (21.7 mmol) under dry nitrogen atmospheric pressure for 24 hr at reflux temperature. Freshly distilled hexane (100 ml) was added to the reaction mixture and insoluble solids in hexane were filtered from the organic solution. After hexane and CS$_2$ were distilled, recrystallization from ether yielded 1.27 g of 9-(trichlorosilyl)methyl-3-phenylfluorene (yield; 15%).

H-NMR(CDCl3, ppm) 2.29(d, J=6.2 Hz, SiCH2, 2H), 4.39(t, 6.4 Hz, CH, 1H), 7.21–7.86(m, ArH, 12H)

Example 5

Reaction of 4-bromobiphenyl with (2,2-dichloroethyl)-trichlorosilane

In the same apparatus and procedures as Example 1 above, 5.0 g (21.7 mmol) of 4-bromobiphenyl and 0.08 g (11.1 mmol) of aluminum foil were alkylated in $CS_2$ (50 ml) solution with (2,2-dichloroethyl)-trichlorosilane 6.68 g (21.7 mmol) for 24 hr. at reflux temperature. Freshly distilled hexane (100 ml) was added to the reaction mixture and insoluble solids in hexane were filtered from the organic solution. After hexane and $CS_2$ were distilled, the reaction products were vacuum distilled to give 1.28 g of 2-bromo-9-(trichlorosilyl)methylfluorene (yield; 15%).

H-NMR(CDCl3, ppm) 2.45(d, J=6.3 Hz, SiCH2, 2H), 4.27(t, 6.0 Hz, CH, 1H), 7.26–7.77(m, ArH, 7H)

Example 6

Reaction of biphenyl with (2,3-dichloropropyl) trichlorosilane

In the same apparatus and procedures as Example 1 above, 6.26 g (40.6 mmol) of biphenyl and 0.54 g (4.1 mmol) of aluminum chloride were alkylated with (2,3-dichloropropyl)trichlorosilane 5.0 g (20.3 mmol) for 2 hr. at 140° C. The aluminum chloride catalyst was quenched with $POCl_3$ and then stirred for another 1 hr. to complete the deactivation. Freshly distilled hexane (50 ml) was added to the reaction mixture and insoluble solids in hexane were filtered from the organic solution. After hexane and biphenyl were distilled, the reaction products were vacuum distilled to give 2.13 g of 9-(2-trichlorosilyl)ethylfluorene (bp; 134°–144° C./0.5 torr, yield; 32%).

H-NMR(CDCl3, ppm) 0.93(t, J=8.4 Hz, SiCH2, 2H), 2.45(m, CH2, 2H), 4.18(t, 4.5 Hz, CH, 1H), 7.26–7.82(m, ArH, 8H)

Example 7

Reaction of para-terphenyl with (3,3-dichloropropyl) trichlorosilane

In the same apparatus and procedures as Example 2 above, 5.0 g (21.7 mmol) of para-terphenyl and 0.22 g (18.2 mmol) of aluminum foil were alkylated in $CS_2$ (30 ml) solution with 6.42 g (26.1 mmol) of (3,3-dichloropropyl) trichlorosilane for 24 hrs at 70° C. Freshly distilled hexane (100 ml) was added to the reaction mixture and insoluble solids in hexane were filtered from the organic solution. After hexane and $CS_2$ were distilled, recrystallization from ether yielded 1.31 g of 9-(3-trichlorosilyl)propyl-2-phenylfluorene (yield; 13%).

H-NMR(CDCl3, ppm) 1.11(t, J=8.4 Hz, SiCH2, 2H), 2.61(m, CH2, 2H), 4.30(t, 4.5 Hz, CH, 1H), 7.52–7.82(m, ArH, 12H)

Example 8

Reaction of 4,4'-dibromobiphenyl with (3,3-dichloropropyl) trichlorosilane

In the same apparatus and procedures as Example 1 above, 5.0 g (16.0 mmol) of 4,4'-dibromobiphenyl and 0.22 g (8.2 mmol) of aluminum foil were alkylated in $CS_2$ (30 ml) solution with 3.9 g (16.0 mmol) of (3,3-dichloropropyl) trichlorosilane for 24 hours at room temperature. The aluminum chloride catalyst was quenched with $POCl_3$ and then stirred for another 1 hr. to complete the deactivation. Freshly distilled hexane (100 ml) was added to the reaction mixture and insoluble solids in hexane were filtered from the organic solution. After hexane and $CS_2$ were distilled, recrystallization from ether yielded 0.93 g of 2,7-dibromo-9-(3-trichloro)propylfluorene (yield;12%).

H-NMR(CDCl3, ppm) 0.95(t, J=8.6 Hz, SiCH2, 2H), 2.40(m, CH2, 2H), 4.11(t, 4.4 Hz, CH, 1H), 7.36–7.64(m, ArH, 6H)

Example 9

Reaction of biphenyl with (2,3-dichlorobutyl) trichlorosilane

In the same apparatus and procedures as Example 1 above, 8.00 g (51.9 mmol) of biphenyl and 0.33 g (2.48 mmol) of aluminum chloride were alkylated with 3.38 g (13.0 mmol) of (2,3-dichlorobutyl)trichlorosilane for 1 hr at 100° C. The aluminum chloride catalyst was quenched with $POCl_3$ and then stirred for another 1 hr. to complete the deactivation. Freshly distilled hexane (50 ml) was added to the reaction mixture and insoluble solids in hexane were filtered from the organic solution. After hexane was distilled, the reaction products were vacuum distilled to give 1.49 g of 9(2-trichlrosilyl)ethyl-9-methylfluorene (bp; 140°–142° C./0.2 torr, yield; 34%).

H-NMR(CDCl3, ppm): 0.60–0.66(m, SiCH2, 2H), 1.54(s, CH3, 2H), 2.24–2.30(m, SiCH2CH2, 2H), 7.34–7.40, 7.74–7.77(m, ArH, 8H)

Example 10

Alkylation of biphenyl with (2,3-dichlorobutyl) methyldichlorosilane

In the same apparatus and procedures as Example 1 above, 2.11 g (13.7 mmol) of biphenyl and 0.20 g (1.58 mmol) of aluminum chloride were alkylated with 1.64 g (6.83 mmol) of (2,3-dichlorobutyl)methyl- dichlorosilane for 1 hour at 100° C. The aluminum chloride catalyst was quenched with $POCl_3$ and then stirred for another 1 hr. to complete the deactivation. Freshly distilled hexane (100 ml) was added to the reaction mixture and insoluble solids in hexane were filtered from the organic solution. After hexane was distilled, the reaction products were vacuum distilled to give 0.20 g of 9-(2-methyldichlorosilyl)ethyl-9-methylfluorene (bp; 138°–140° C./0.2 torr, yield; 9%).

H-NMR(CDCl3, ppm): 0.67(s, SiCH3, 3H), 1.08–1.18(m, SiCH2, 2H), 1.61(s, CH3, 2H), 2.28–2.33(m, SiCH2, 2H), 7.31–7.83(m, ArH, 8H)

What is claimed is:

1. (Fluorenylalkyl)silanes represented by formula (I)

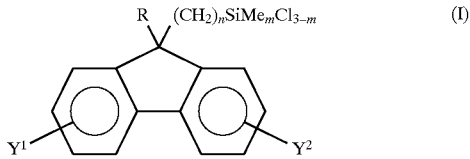

(wherein m is 0 or 1; n is 0, 1, or 2; and $Y^1$ and $Y^2$ which may be same or different represent hydrogen, bromo, or phenyl).

2. A method for preparing (fluorenylalkyl)silanes represented by formula (I) by reacting substituted biphenyl represented by formula (II) with (dichloroalkyl)silanes represented by formula (III) in the presence of Lewis acid catalyst at the reaction temperature between 0° and 200° C.

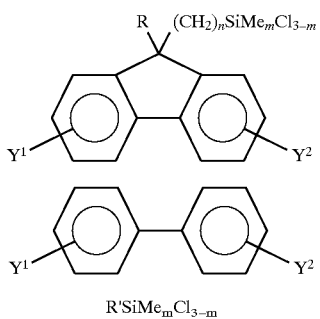

(I)

(II)

R'SiMe$_m$Cl$_{3-m}$ (III)

(wherein m is 0 or 1; n is 0, 1, or 2; $Y^1$ and $Y^2$ which may be same or different represent hydrogen, bromo, or phenyl; R represents hydrogen or methyl group; and R' can be dichloromethyl, 2,2-dichloroethyl, 3,3-dichloropropyl, 1,2-dichloroethyl, 2,3-dichloropropyl, 2,3-dichlorobutyl).

3. The method according to claim 2 wherein the Lewis acid is aluminum chloride or aluminum.

4. The method according to claim 3 wherein the amount of Lewis acid is 1–100 mol percent of polychlorinated alkylsilanes represented by formula (III).

* * * * *